United States Patent [19]

Thompson

[11] Patent Number: 5,589,482
[45] Date of Patent: Dec. 31, 1996

[54] BENZO-THIOPHENE ESTROGEN AGONISTS TO TREAT PROSTATIC HYPERPLASIA

[75] Inventor: David D. Thompson, Groton, Conn.

[73] Assignee: Pfizer Inc., New York, N.Y.

[21] Appl. No.: 356,011

[22] Filed: Dec. 14, 1994

[51] Int. Cl.$^6$ .......... A61K 31/44; A61K 31/445; A61K 31/395; A61K 31/40
[52] U.S. Cl. .......... 514/305; 324/212; 324/210; 324/422; 324/448
[58] Field of Search .......... 514/443, 324, 514/422, 578, 210, 448, 470, 418, 305, 212

[56] References Cited

U.S. PATENT DOCUMENTS

| | | | |
|---|---|---|---|
| 4,133,814 | 1/1979 | Jones et al. | 260/326.55 |
| 4,358,593 | 11/1982 | Jones et al. | 546/202 |
| 4,380,635 | 4/1983 | Peters | 546/202 |
| 4,418,068 | 11/1983 | Jones et al. | 424/267 |
| 4,732,912 | 3/1988 | Pilgrim et al. | 514/510 |
| 4,859,585 | 8/1989 | Sonnenschein et al. | 435/29 |
| 4,970,237 | 11/1990 | Jensen et al. | 514/651 |
| 5,021,414 | 6/1991 | Pilgrim et al. | 514/237.5 |
| 5,075,321 | 12/1991 | Schreiber et al. | 514/317 |
| 5,147,880 | 9/1992 | Jones et al. | 514/319 |
| 5,196,435 | 3/1993 | Clemens et al. | 514/284 |
| 5,393,763 | 2/1995 | Black et al. | 514/333 |

FOREIGN PATENT DOCUMENTS

| | | |
|---|---|---|
| 2123514 | 5/1993 | Canada. |
| 0062504 | 10/1982 | European Pat. Off.. |
| 0062503 | 10/1982 | European Pat. Off.. |
| 0516257 | 2/1992 | European Pat. Off.. |
| 0584952 | 3/1994 | European Pat. Off.. |
| 9310113 | 10/1993 | Japan. |
| 9310741 | 6/1993 | WIPO. |
| 9510513 | 4/1995 | WIPO. |

OTHER PUBLICATIONS

Marsh, et al. "Management of Menopause" British Medical Bulletin (1992), vol. 48, No. 2 pp. 426–428.

Prince, et al. "Prevention of Postmenopausal Osteoporosis" The New England Journal of Medicine, Oct. 14, 1991 vol. 325, No. 17 pp. 1190–1193.

Nabulshi, et al. "Association of Hormone–Replacement Therapy with Various Cardiovascular Rish Factors in Pos–Menopausal Women" The New England Journal of Medicine Apr. 15, 1993, vol. 328 No. 15, pp. 1069–1075.

Tikkanen, et al. "Natural Estrogen as an Effective Treatment for Type–II Hyperlipoproteinaemia in Postmenopausal Women" The Lancet, Sep. 2, 1978, pp. 490–493.

Osteoporosis Conference, Script No. 1812/13 Apr. 16th/20th 1993, pp. 29–30 PJB Publishers Ltd.

Jones, et al. "Antiestrogens.2.$^1$ Activity Studies in a Series of 3-Aroyl-2-arylbenzo[b]thiophene Derivatives Leading to [6–Hydroxy-2-(4–hydroxyphenyl)benzol[b]theine-3-yl] [4-2-(2-piperidinyl) ethoxy]-phenyl]methanone Hydrochloric (LY156758), a Remarkably Effective Estrogen Antagonist with only Minimal Intrinsic Estrocgencity" J. Med. Chem., 1984, 27, 1057–1066.

Hong, et al. "Effects of Estrogen Replacement Therapy on Serum Lipid Values and Angiographically Defined Coronary Artery Disease in Postmenopausal Women" The American Journal of Cardiology, Jan. 15, 1992 vol. 69 pp. 176–178.

Recker, Robert R., Clinical Review 41, Current Therapy for Osteoporosis, Journal of Clinical Endocrinology and Metabolism vol. 76, No. 1 pp. 14–16, 1991.

Carter, S. K. et al, Chemotherapy of Cancer, 2$^{nd}$ Edition, pp. 361–365, (1987).

Primary Examiner—Theodore J. Criares
Attorney, Agent, or Firm—Peter C. Richardson; Gregg C. Benson; Mervin E. Brokke

[57] ABSTRACT

Benzothiophenes and related compounds of the formula

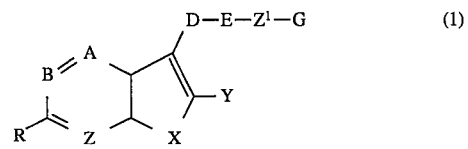

(1)

are estrogen agonists which are useful for treating prostatic and diseases, obesity and bone loss in male animals.

10 Claims, No Drawings

BENZO-THIOPHENE ESTROGEN AGONISTS TO TREAT PROSTATIC HYPERPLASIA

BACKGROUND OF THE INVENTION

The value of naturally occurring estrogens and synthetic compositions demonstrating "estrogenic" activity has been in their medical and therapeutic uses. A traditional listing of the therapeutic applications for estrogens alone or in combination with other active agents includes: oral contraception; relief for the symptoms of menopause; prevention of threatened or habitual abortion; relief of dysmenorrhea; relief of dysfunctional uterine bleeding; an aid in ovarian development; treatment of acne; diminution of excessive growth of body hair in women (hirsutism); the prevention of cardiovascular disease; treatment of osteoporosis; treatment of prostatic carcinoma; and suppression of post-partum lactation [Goodman and Gilman, The Pharmacological Basis Of Therapeutics (Seventh Edition) Macmillan Publishing Company, 1985, pages 1421–1423]. Accordingly, there has been increasing interest in finding newly synthesized compositions and new uses for previously known compounds which are demonstrably estrogenic, that is, able to mimic the action of estrogen in estrogen responsive tissue.

From the viewpoint of pharmacologists interested in developing new drugs useful for the treatment of human diseases and specific pathological conditions, it is most important to procure compounds with some demonstrable estrogen-like function but which are devoid of proliferative side-effects. Exemplifying this latter view, osteoporosis, a disease in which bone becomes increasingly more fragile, is greatly ameliorated by the use of fully active estrogens; however, due to the recognized increased risk of uterine cancer in patients chronically treated with active estrogens, it is not clinically advisable to treat osteoporosis in intact women with fully active estrogens for prolonged periods. Accordingly estrogen agonists are the primary interest and focus.

There is a need for improved estrogen agonists which exert selective effects on different tissues in the body. Tamoxifen, 1-(4-β-dimethylaminoethoxyphenyl)-1,2-diphenyl-but-1-ene, is an antiestrogen which has a palliative effect on breast cancer, but is reported to have estrogenic activity in the uterus.

Gill-Sharma, et al., *J. Reproduction and Fertility* (1993) 99, 395, disclose that tamoxifen at 200 and 400 mg/kg/day reduces the weights of the testes and secondary sex organs in male rats.

Recently it has been reported (Osteoporosis Conference Scrip No. 1812/13 Apr. 16/20, 1993, p29) that raloxifene, 6-hydroxy-2-(4-hydroxyphenyl)-3-[4-(2-piperidinoethoxy)benzoyl]benzo[b] thiophene, mimics the favorable action of estrogen on bone and lipids but, unlike estrogen, has minimal uterine stimulatory effect. (Breast Cancer Res. Treat. 10(1). 1987 p 31–36 Jordan, V. C. et al.)

Neubauer, et al., *The Prostate* 23:245 (1993) teach that raloxifene treatment of male rats produced regression of the ventral prostate.

Raloxifene as well as ethers and esters thereof and related compounds are described as antiestrogen and antiandrogenic materials which are effective in the treatment of certain mammary and prostate cancers. See U.S. Pat. No. 4,418,068 and Charles D. Jones, et al., J. Med. Chem. 1984, 27, 1057–1066.

Jones, et al in U.S. Pat. No. 4,133,814 describe derivatives of 2-phenyl-3-aroylbenzothiophene and 2-phenyl-3-aroyl-benzothiophene-1-oxides which are useful as antifertility agents as well as suppressing the growth of mammary tumors.

Related 2-phenyl-3-aroylbenzothiophenes have also been claimed to modulate the clearance of antibody coated cells from the circulation of mammals, thus providing a method of treating autoimmune disease, U.S. Pat. No. 5,075,321.

SUMMARY OF INVENTION

This invention provides a method of treating benign prostate hyperplasia and prostatic carcinoma which comprises administering to a mammal suffering from prostatic disease a therapeutically effective amount of a compound of the formula

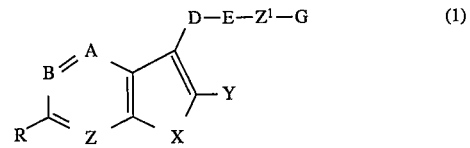 (1)

wherein
A, B and Z are independently
(a) —OH=,
(b) —CR$^4$=,
(c) =N—;
X is
(a) —S—,
(b) —O—,
(c) —NH—,
(d) —NR$^2$—,
(e) —CH$_2$CH$_2$—,
(f) —CH$_2$CH$_2$CH$_2$—,
(g) —CH$_2$O—,
(h) —OCH$_2$—,
(i) —CH$_2$S—,
(j)

(k) —SCH$_2$—,
(l) —N=CR$^2$—,
(m) —R$^2$C=N—;
Y is
(a) phenyl, optionally substituted with 1–3 substituents independently selected from the group consisting of halo, hydroxy, C$_1$–C$_4$ alkyl, C$_1$–C$_4$ alkoxy,

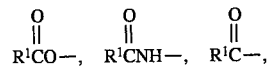

and R$^1$SO$_2$NH—;
(b) C$_1$–C$_8$ alkyl, said alkyl groups being optionally substituted with 1–3 substituents independently selected from the group consisting of —OH, —OR$^2$,

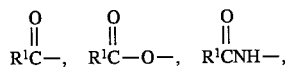

and R$^1$SO$_2$NH—;

(C) $C_3$–$C_8$ cycloalkyl, optionally substituted with 1–2 substituents independently selected from the group consisting of —OH, —$R^1$, —$NH_2$,

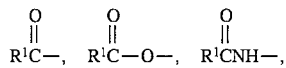

and $R^1SO_2NH$—;

(d) $C_3$–$C_8$ cycloalkenyl, optionally substituted with 1–2 substituents independently selected from the group consisting of —OH,

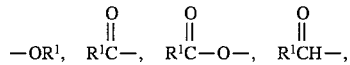

and $R^1SO_2NH$—;

(e) a five membered heterocycle containing up to two heteroatoms selected from the group consisting of —O—, —$NR^2$—, and —$S(O)_n$—, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, aryl ($C_1$–$C_4$)alkyl, —$CO_2H$, —CN, —$CONHOR^1$, —$SO_2NHR^1$, —$NH_2$, $C_1$–$C_4$ alkylamino, $C_1$–$C_4$ dialkylamino, —$NHSO_2R^1$, —$NHCOR^1$, —$NO_2$, and -aryl;

(f) a six membered heterocycle containing up to two heteroatoms selected from the group consisting of —O—, —$NR^2$— and —$S(O)_n$— optionally substituted with 1 to 3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, aryl ($C_1$–$C_4$)alkyl, —$CO_2H$, —CN, —$CONHOR^1$, —$SO_2NHR^1$, —$NH_2$, $C_1$–$C_4$ alkylamino, $C_1$–$C_4$ dialkylamino, —$NHSO_2R^1$, —$NHCOR^1$, —$NO_2$, and —aryl;

(g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$alkylsulfinyl, $C_1$–$C_4$ alkylsulfonyl, hydroxy ($C_1$–$C_4$)alkyl, aryl ($C_1$–$C_4$)alkyl, —$CO_2H$, —CN, —$CONHOR^1$, —$SO_2NHR^1$, —$NH_2$, $C_1$–$C_4$ alkylamino, $C_1$–$C_4$ dialkylamino, —$NHSO_2R^1$, —$NHCOR^1$, —$NO_2$, —OH, and —aryl;

D is (a) —CO—,
(b) —$CR_2R^3$—,
(c) —CONH—,
(d) —NHCO—,
(e) —$CR^2(OH)$—,
(f) —$CONR^2$—,
(g) —$NR^2CO$—, (h) 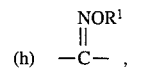

(i) 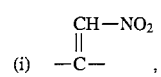

(j) 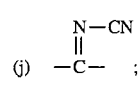

E is (a) a single bond;

(b) phenyl, or phenyl substituted with up to three substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, aryl ($C_1$–$C_4$)alkyl, —$CO_2H$, —CN, —CONHOR, —$SO_2NHR$, —$NH_2$, $C_1$–$C_4$ alkylamino, $C_1$–$C_4$ dialkylamino, —$NHSO_2R$, —$NHCOR^1$, —$NO_2$, and -aryl; or (c) a 5 or 6 membered heterocycle, optionally fused to a phenyl ring containing up to two heteroatoms selected from the group consisting of —O—, —$NR^2$— and —$S(O)_n$— optionally substituted with 1–3 substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, aryl ($C_1$–$C_4$) alkyl, —$CO_2H$, —CN, —CONHOR, —$SO_2NHR$, —$NH_2$, $C_1$–$C_4$ alkylamino, $C_1$–$C_4$ dialkylamino, —$NHSO_2R$, —$NHCOR^1$, —$NO_2$, and -aryl;

$Z^1$ is (a) —$(CH_2)_p$ W$(CH_2)_q$—,
(b) —$O(CH_2)_p$ $CR^5$ $R^6$—,
(c) —$O(CH_2)_p$W$(CH_2)_q$;

G is (a) —$NR^7$ $R^8$, (b)

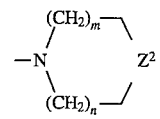

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a substituent selected from (1) —$OR^1$, (2) —$SO_2NR^2R^3$, (3) 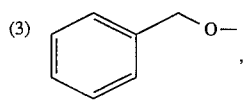

(4) 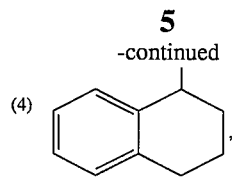

(5) halogen, (6) 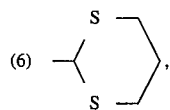

(7) 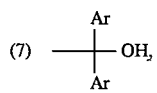

(8) 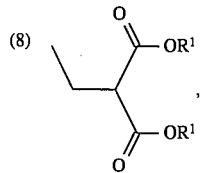

(9) 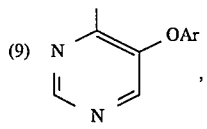

(10) 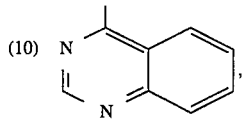

(11) 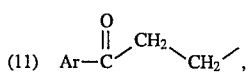

(12) 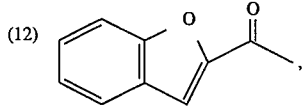

(13) $-C\equiv CR^1$,

(14) 

(15) 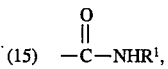

(16) 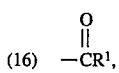

(17) 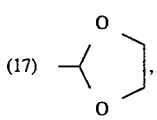

(18) $Ar-CH_2-$,

(19) 

(20) 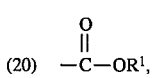

(21) $-(CF_2)_mCF_3$,

(22) 

(c) 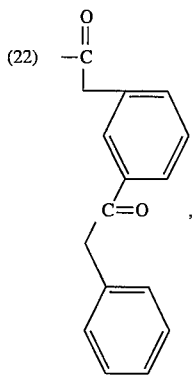

(d) 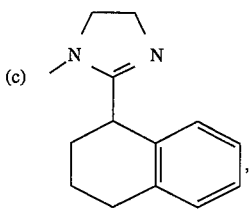

(e) a 5 or 6 membered heterocycle containing up to two heteroatoms selected from the group consisting of $-O-$, $-NR^2-$ and $-S(O)_n-$ optionally substituted with 1–3 substituents independently selected from the group consisting of hydrogen, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy $(C_1-C_4)$alkyl, aryl $(C_1-C_4)$alkyl, $-CO_2H$, $-CN$, $-CONHOR$, $-SO_2NHR$, $-NH_2$, $C_1-C_4$ alkylamino, $C_1-C_4$ dialkylamino, $-NHSO_2R$, $-NHCOR^1$, $-NO_2$, and -aryl; said heterocycle being joined to group $Z^1$ by a carbon to carbon bond or carbon-nitrogen bond;

(f) a bicyclic amine containing a five to twelve carbon atoms, either bridged or fused and optionally substituted with 1–3 substituents independently selected from the group consisting of hydrogen, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy $(C_1-C_4)$alkyl, aryl $(C_1-C_4)$alkyl, $-CO_2H$, $-CN$, $-CONHOR$, $-SO_2NHR$, $-NH_2$, $C_1-C_4$ alkylamino, $C_1-C_4$ dialkylamino, $-NHSO_2R$, $-NHCOR^1$, $-NO_2$, and $-$aryl; $Z^1$ and G in combination may be

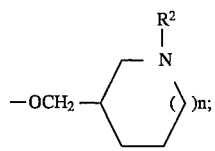

Ar is phenyl or naphthyl optionally substituted with up to three substituents independently selected from $R^4$;

W is (a) —$CH_2$—,
(b) —CH=CH—,
(c) —O—,
(d) —$NR^2$—,
(e) —$S(O)_n$—,

(g) —$CR_2(OH)$—,
(h) —$CONR^2$—,
(i) —$NR_2CO$—,
(j)

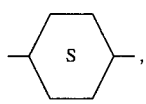

(k) —C≡C—;
R is
(a) halogen,
(b) —$NR^3R^2$,
(c) —$NHCOR^2$,
(d) —$NHSO_2R^2$,
(e) —$CR^2R^3OH$,
(f) —$CONR_2R^3$,
(g) —$SO_2NR^2R^3$,
(h) hydroxyl,
(i) $R^1O$—,

$R^1$ is $C_1$–$C_6$ alkyl or phenyl optionally substituted with up to three substituents independently selected from $C_1$–$C_6$ alkyl, halogen, $C_1$–$C_6$alkoxy, hydroxy and carboxy;
$R^2$ and $R^3$ are independently
(a) hydrogen
(b) $C_1$–$C_4$ alkyl;
$R^4$ is
(a) hydrogen,
(b) halogen,
(c) $C_1$–$C_4$ alkyl,
(d) $C_1$–$C_4$ alkoxy,
(e) $C_1$–$C_4$ acyloxy,
(f) $C_1$–$C_4$ alkylthio,
(g) $C_1$–$C_4$ alkylsulfinyl,
(h) $C_1$–$C_4$ alkylsulfonyl,
(i) hydroxy ($C_1$–$C_4$)alkyl,
(j) aryl ($C_1$–$C_4$)alkyl,
(k) —$CO_2H$,
(l) —CN,
(m) —CONHOR,
(n) —$SO_2NHR$,
(o) —$NH_2$,
(p) $C_1$–$C_4$ alkylamino,
(q) $C_1$–$C_4$ dialkylamino,
(r) —$NHSO_2R$,
(s) —$NO_2$,
(t) —aryl;
$R^5$ and $R^6$ are independently $C_1$–$C_8$ alkyl or together form a $C_3$–$C_{10}$ carbocyclic ring;
$R^7$ and $R^8$ are independently
(a) phenyl,
(b) a $C_3$–$C_{10}$ carbocyclic ring, saturated or unsaturated,
(c) a $C_3$–$C_{10}$ heterocyclic ring containing up to two heteroatoms, selected from —O—, —N— and —S—
(d) H,
(e) $C_1$–$C_6$ alkyl,
(f) or form a 3 to 8 membered nitrogen containing ring with $R^5$ or $R^6$; $R^7$ and $R^8$ in either linear or ring form may optionally be substituted with up to three substituents independently selected from $C_1$–$C_6$ alkyl, halogen, alkoxy, hydroxy and carboxy;
a ring formed by $R^7$ and $R^8$ may be optionally fused to a phenyl ring;
m is 1, 2 or 3;
n is 0, 1 or 2;
p is 0, 1, 2 or 3;
q is 0, 1, 2, or 3;
and geometric and optical isomers, pharmaceutically acceptable salts thereof.

This invention provides a method of treating prostatic diseases with preferred groups of compounds of formula 1 wherein
1. R is —OH.
2. A, B and Z are independently selected from —CH= and —CF=.
3. X is —S—.
4. D is —CO— or $CH_2$—.
5. E is 1,4-linked phenyl, pyridyl, pyrimidine,

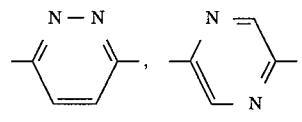

6. $Z^1$ is —$OCH_2CH_2$—, —$CH_2CH_2$—, —$CH_2$—,

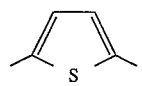

C≡C—$CH_2$—, or Z in combination with G is

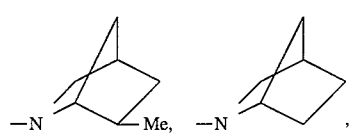

7. G is

-continued

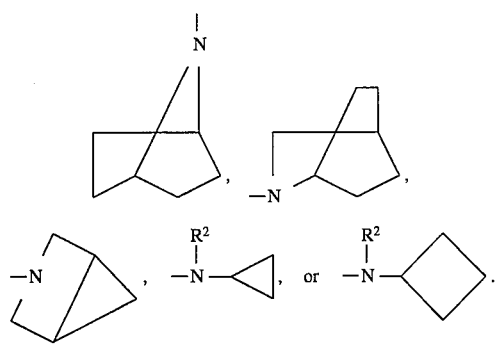

8. R is —OH; A, B and Z are —CH—; X is S; Y is

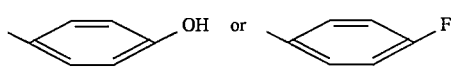

D is $-\overset{O}{\overset{\|}{C}}-$ or $-CH_2-$,

E is  or 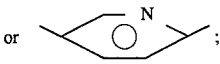;

$Z^1$ is $-CH_2-CH_2-CH_2-$ or $-OCH_2-\overset{R^2}{\overset{|}{CH}}-$.

A further preferred group of compounds for the treatment of prostatic disease are those of formula 1 wherein:

A, B and Z are —CH=;

X is —S—;

Y is phenyl, 4-hydroxyphenyl, 4-chlorophenyl, 4-fluorophenyl,

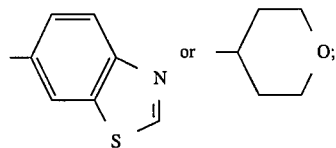

R is —OH—;

D is —CO— or —CH$_2$—;

E is phenyl or pyridyl; and $Z^1$ is —OCH$_2$CH$_2$—, —C≡C—CH$_2$—, —OCH$_2$—, or —NHCH$_2$CH$_2$—.

Further preferred with the above group are those compounds wherein: G is

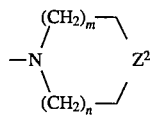

wherein n is 0, 1 or 2;

m is 1, 2 or 3 and $Z^2$ is —NH—, —O—, —S— or —CH$_2$—.

Or those compounds wherein G is:

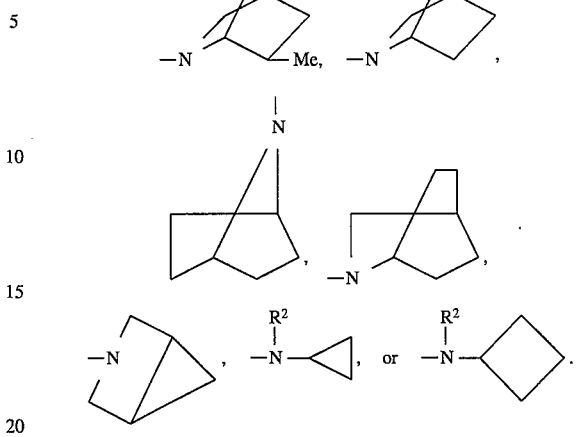

Or those compounds wherein G is:

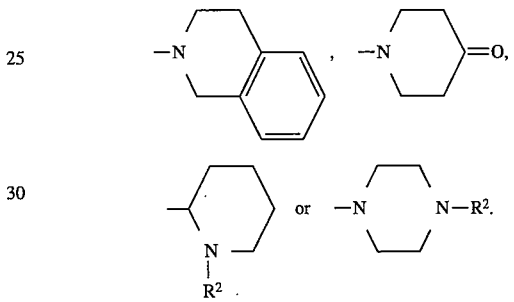

In another aspect this invention provides a method of treating bone loss in a male mammal which comprises administering to said male mammal an amount of a compound of formula 1 and preferred groups of formula 1 compounds as described above which is effective in preventing bone loss.

In another aspect this invention provides a method of treating or preventing obesity in mammals which comprises administering to said mammal an amount of a compound of formula 1 and preferred groups of formula 1 compounds as described above which is effective in treating or preventing obesity.

DETAILED DESCRIPTION OF THE INVENTION

This preparation of the compounds of formula 1 is described in commonly owned, co-pending U.S. patent application Ser. No. 08/135,386 which is incorporated herein by reference.

As used in this application, prostatic disease means benign prostatic hyperplasia or prostatic carcinoma.

Bone mineral density, a measure of bone mineral content, accounts for greater than 80% of a bone's strength. Loss of bone mineral density with age and/or disease reduces a bone's strength and renders it more prone to fracture. Bone mineral content is accurately measured in people and animals by dual x-ray absorptiometry (DEXA) such that changes as little as 1% can be quantified. We utilize DEXA to evaluate changes in bone mineral density due to androgen deficiency following orchidectomy (surgical removal of testes) and treatment with vehicle, testosterone, or estrogen agonists of the present invention.

Pharmaceutical formulations for the treatment of prostatic diseases, obesity and bone loss of this invention comprise, as active ingredient, a compound of formula I or a salt thereof. The pharmaceutically acceptable salts of the compounds of formula I are salts of non-toxic type commonly used, such as salts with organic acids (e.g., formic, acetic, trifluoroacetic, citric, maleic, tartaric, methanesulfonic, benzenesulfonic or toluenesulfonic acids), inorganic acids (e.g. hydrochloric, hydrobromic, sulfuric or phosphoric acids), and amino acids (e.g., aspartic or glutamic acids). These salts may be prepared by the methods known to chemists of ordinary skill.

The remedies for prostatic diseases, obesity and bone loss of this invention may be administered to animals including humans orally or parenterally in the conventional form of preparations, such as capsules, microcapsules, tablets, granules, powder, troches, pills, suppositories, injections, suspensions and syrups.

The remedies for prostatic diseases, obesity and bone loss of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutic effect; for example, about 1 mg to 100 mg in unit dosage for both oral and parenteral administration.

The active ingredient may be usually administered once to four times a day with a unit dosage of 0.25 mg to 100 mg in human patients, but the above dosage may be properly varied depending on the age, body weight and medical condition of the patient and the type of administration. One dose per day is preferred.

Pharmaceutical chemists will easily recognize that physiologically active compounds which have accessible hydroxy groups are frequently administered in the form of pharmaceutically acceptable esters or ethers. The literature concerning such compounds, such as estradiol, provides a great number of instances of such esters and ethers. The compounds of this invention are no exception in this respect, and can be effectively administered as an ether or ester, formed on the hydroxy groups, just as one skilled in pharmaceutical chemistry would expect. While the mechanism has not yet been investigated, it is believed that ethers and esters are metabolically cleaved in the body, and that the actual drug, which such form is administered, is the hydroxy compound itself. It is possible, as has long been known in pharmaceutical chemistry, to adjust the rate or duration of action of the compound by appropriate choices of ester or ether groups. For example, the cycloalkyl ethers are known to increase the duration of action of many hydroxy-group-bearing physiologically active compounds.

Certain ether and ester groups are preferred as constituents of the compounds of this invention. The compounds of formula I may contain ester or ether groups at various portions as defined herein above, where these groups are represented as —$COOR^9$, and —$OR^{10}$;

$R^9$ is $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri (chloro or fluoro)methyl;

$R^{10}$ is $C_1$–$C_4$ alkyl, $C_5$–$C_7$ cycloalkyl or benzyl; and the pharmaceutically acceptable acid addition salts thereof.

The pharmaceutically acceptable acid addition salts of the compounds of this invention may be formed of the compound itself, or of any of its esters or ethers, and include the pharmaceutically acceptable salts which are often used in pharmaceutical chemistry. For example, salts may be formed with inorganic or organic acids such as hydrochloric acid, hydrobromic acid, hydriodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid. It is usually preferred to administer a compound of this invention in the form of an acid addition salt, as it is customary in the administration of pharmaceuticals bearing a basic group such as the piperidino ring.

The following Examples will serve to illustrate, but do not limit the invention which is defined by the claims.

EXAMPLE 1

Effect on Prostate Weight

Male rats (3½ months old) are sham-operated or orchidectomized under ketamine-xylazine anesthesia. Upon recovery the next day, daily subcutaneous dosing is begun with either vehicle, testosterone (1 mg/kg) or a compound of the present invention (300 μg/kg) for 2 weeks. At sacrifice, animals are bled by cardiac puncture. Prostate weights are determined.

In sham-operated rats, prostate weights are significantly reduced at 2 weeks in animals dosed with a compound of the present invention. In animals which have undergone orchidectomy, prostate weights are drastically reduced but are restored by the addition of testosterone.

EXAMPLE 2

Bone Mineral Density

Male rats (3½ months old) are sham-operated or orchidectomized under ketamine-xylazine anesthesia. Upon recovery the next day, daily subcutaneous dosing is begun with either vehicle, testosterone (1 mg/kg) or a compound of the present invention (300 μg/kg) for 2 weeks. After 14 days the rats are killed and femora removed and defleshed. The femora are positioned on a Hologic QDR1000W (Hologic, Inc., Waltham, Mass.) and bone mineral density is determined in the distal portion of the femur at a site from 1 cm to 2 cm from the distal end of the femur using the high resolution software supplied by Hologic. Bone mineral density is determined by dividing the bone mineral content by the bone area of the distal femur. Each group contains at least 6 animals. Mean bone mineral density is obtained for each animal and statistical differences (p<0.05) from the vehicle-treated orchidectomized and sham-operated group are determined by t test.

EXAMPLE 3

Effect on Obesity

Sprague-Dawley female rats at 10 months of age, weighing approximately 450 grams, are sham-operated (sham) or ovariectomized (OVX) and treated orally with vehicle, 17α ethynyl estradiol at 30 µg/kg/day or a compound of formula I at 1.0, 2.5 or 5 mg/kg/day for 8 weeks. There are 6 to 7 rats in each sub group. On the last day of the study, body composition of all rats is determined using dual energy x-ray absorptiometry (Hologic QDR-1000/W) equipped with whole body scan software which shows the proportions of fat body mass and lean body mass.

A decrease in fat body mass indicates that the estrogen agonists of formula I are useful in preventing and treating obesity.

I claim:

1. A method of treating prostatic hyperplasia in a mammal which comprises administering to a mammal in need of such treatment a compound of the formula

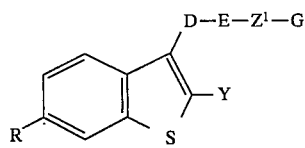

wherein:
R is $OR^1$ wherein $R^1$ is hydrogen, $C_1$–$C_6$ alkyl or phenyl optionally substituted with up to three substituents independently selected from $C_1$–$C_6$ alkyl, $C_1$–$C_6$ alkoxy or halogen;

Y is phenyl, optionally substituted with 1 to 3 substituents independently selected from halo, hydroxy and $C_1$–$C_4$ alkyl;

D is —CO— or —$CH_2$—;

E is 1,4 linked phenylene;

$Z^1$ is —$OCH_2CH_2$—, —$CH_2CH_2$—, —$CH_2$—, —$OCH_2CHR^2$—, —C≡C—$CH_2$—; or $Z^1$ in combination with G is

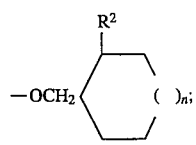

G is 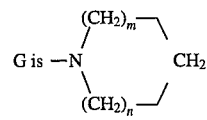

wherein n is 0, 1 or 2; m is 1, 2 or 3; or G is azabicyclohept-2-yl; or G in combination with $Z^1$ is

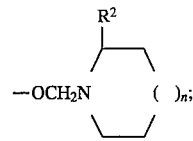

and geometric and optical isomers pharmaceutically acceptable esters, ethers and salts thereof.

2. The method of claim 1 in which the compound of formula I is {4-[2-(2-Aza-bicyclo[2.2.1]hept-2-yl)-ethoxy]-phenyl}-[6-hydroxy-2-(4-hydroxy-phenyl)benzo[b]thiophen-3-yl]-methanone.

3. The method of claim 1 in which the compound of formula I is [6-Hydroxy-2-(4-hydroxy-phenyl)-benzo[b]thiophen-3-yl]-[4-(1-methyl-2-piperidin-1-yl-ethoxy)-phenyl]methanone.

4. The method of claim 1 in which the compound of formula I is [6-Hydroxy-2-(4-hydroxy-phenyl)-benzo[b]thiophen-3-yl]-[4-(1-methyl-piperidin-2-yl-methoxy)-phenyl]methanone.

5. The method of claim 1 in which the compound of formula I is [2-(4-Fluoro-phenyl)-6-hydroxy-benzo[b]thiophen-3-yl]-[4-(2-piperidin-1-yl-ethoxy)-phenyl]methanone.

6. The method of claim 1 in which the compound of formula I is [6-Hydroxy-2-(4-hydroxy-phenyl)-benzo[b]thiophen-3-yl]-[4-(3-piperidin-1-yl-prop-1-ynyl)-phenyl]methanone.

7. The method of claim 1 in which the compound of formula I is 2-(4-Hydroxy-phenyl)-3-[4-(2-piperidin-1-yl-ethoxy)-benzyl]-benzo[b]thiophen-6-ol.

8. The method of claim 1 in which the compound of formula I is [4-(2-Cyclobutylamino-ethoxy)-phenyl]-[6-hydroxy-2-(4-hydroxy-phenyl)-benzo[b]thiophen-3-yl]-methanone.

9. The method of claim 1 in which the compound of formula I is [4-(1-Ethyl-piperidin-2-ylmethoxy)-phenyl]-[6-hydroxy-2-(4-hydroxy-phenyl)-benzo[b]thiophen-3yl]-methanone.

10. The method of claim 1 in which the compound of formula I is [6-Hydroxy-2-(4-hydroxy-phenyl)-benzo[b]thiophen-3-yl]-{4-[2-(6-methyl-2-aza-bicyclo[2.2.1]hept-2-yl)ethoxy]-phenyl}-methanone.

* * * * *